United States Patent [19]

Pachence

[11] Patent Number: 5,157,111

[45] Date of Patent: Oct. 20, 1992

[54] METHOD OF BONDING COLLAGEN TO FIBERS, PARTICULARLY DACRON

[76] Inventor: James M. Pachence, 7 Chopin La., Lawrenceville, N.J. 08648

[21] Appl. No.: 694,729

[22] Filed: May 2, 1991

[51] Int. Cl.$^5$ ................................................ C07K 3/08
[52] U.S. Cl. ............................ 530/356; 128/DIG. 8; 428/373; 530/354; 623/1
[58] Field of Search ............... 530/356, 410, 322, 323, 530/362; 128/DIG. 8; 428/373; 525/54.1; 623/1, 11, 13, 16, 23

[56] References Cited

U.S. PATENT DOCUMENTS

| | | | |
|---|---|---|---|
| 3,098,693 | 7/1963 | Sheehan | 530/354 |
| 3,276,448 | 10/1966 | Kronenthal | 623/1 |
| 4,115,301 | 9/1978 | Hornby et al. | 525/54.1 |

Primary Examiner—Merrell C. Cashion, Jr.
Assistant Examiner—P. Lynn Touzeau
Attorney, Agent, or Firm—Caesar, Rivise, Bernstein, Cohen & Pokotilow, Ltd.

[57] ABSTRACT

A method of bonding collagen to synthetic polyester fibers, particularly DACRON. The method involves providing synthetic polyester fabric fibers having repeating carbonyl groups, hydrogenating the repeating carbonyl groups and then conducting a transesterification step which includes the addition of free amine groups. The free amine groups are reacted with a bifunctional crosslinking agent to produce modified polyester fibers. The final step involves adding collagen to the modified polyester fibers for a time sufficient to produce covalent bonding of the collagen to the fibers.

The invention also involves the making of a fabric matrix comprised of synthetic polyester fibers, particularly DACRON, and collagen being covalently bound to the fibers. Such matrix can be utilized in ligament prosthesis design.

8 Claims, 3 Drawing Sheets

METHOD OF BONDING COLLAGEN TO FIBERS, PARTICULARLY DACRON

This invention relates to a method of bonding collagen to fibers, particularly dacron. As will be seen the invention also relates to the finished product itself which is to be utilized in the fabrication of various novel ligament prostheses.

The repair of injured tendons and ligaments has presented unique challenges from both a surgical and a materials point of view. Current repair techniques using either naturally occurring materials or synthetic materials have shown limited success due to such negative factors as extended recovery time, painful rehabilitation, and a high rate of stretching and frank failure. In addition, inadequate repair of tendon and ligament damage may lead to degenerative changes to joints, with subsequent arthritic conditions.

One promising concept for the repair of tendon and ligament damage followed by several investigators is the augmentation of autogenous grafts to provide temporary mechanical integrity until new tissue can assume normal mechanical functions. Alternatively, there are considerations of finding or developing a material which has an initial strength exceeding that of a normal tendon or ligament and which simultaneously encourages the growth of new, organized fibrous tissue for long-term stability.

With the fabrication of a novel ligament prosthesis incorporating several key concepts into the device design, the mechanical characteristics of the device are expected to be initially equal to or greater than normal connective tissue due to the initial mechanical properties of the synthetic fiber. Moreover, with the present invention, a collagen surface covalently bonded to the synthetic fibers of the implant serves as a matrix for new fibrous tissue growth, as fibroblasts will readily attach to type I collagen. Moreover, the fibrous tissue deposited on the implant will have mechanical and morphological features similar to normal collagenous tissue. The bone attachment site of the ligament prosthesis serves to encourage bone ingrowth. The ligament prosthesis design takes into account varying tension modes as a function of knee extension.

With the present invention, there is established a chemical procedure to covalently link collagen to DACRON, a synthetic fiber used extensively in implantable medical devices. An in vitro assay shows that the collagen-coated DACRON composite encourages cell attachment and growth of fibroblasts to a greater degree than DACRON alone.

In addition, an in vivo biocompatibility assay was used to compare the DACRON-collagen composite with DACRON alone; it was found that the collagen coating improved the cellular response to the implant as well as improved the connective tissue production around the implant when compared to simple DACRON fibers.

There is also a method to attach calcium hydroxyapatite (HA) to the collagen-coated DACRON fibers. The HA coating will be used on the ends of the prosthesis, which is anticipated to promote bone ingrowth at the attachment sites.

BACKGROUND OF THE INVENTION

The footnotes set forth hereinbelow are listed in detail at the end hereof.

The study of tendon and ligament injury, and the subsequent treatment of such injuries, has led to numerous techniques for the repair, augmentation, or replacement of this injured tissue. Numerous techniques have called for the use of naturally occurring materials (such as autografts allografts, and xenografts, or synthetic materials (for example, carbon fibers, DACRON, or other polymers. However, many investigators have stated that no one technique can be called ideal. The repair of tendon and ligament injury is difficult at best, and these technical problems lead to prolonged recovery periods (often greater than one year), painful rehabilitation, and possibly impairment of function; for example, inadequate repair of the anterior cruciate ligament results in degenerative changes to the knee, possibly leading to arthritic conditions.

The complete replacement of ligaments has been a challenging materials problem, as the materials must (1) be biocompatible; (2) have sufficient mechanical strength; (3) have resilience to withstand millions of fatigue cycles associated with normal ligament use; (4) withstand the biochemical and physiological environment; and (5) support the growth of new connective tissue. To date, several synthetic materials have been found to be biocompatible and to support fibroblast growth to some extent however, synthetic materials have demonstrated a susceptibility to stretching, fatigue, and shear and other stresses that lead to device failure. Naturally occurring collagenous material, such as autografts, allografts, or xenografts, also have limitations. Ligament repair with autogenous tissue has been used successfully for many years, but its use is not always possible, especially when trauma or disease is severe.

In addition, histological studies of autogenous grafts indicate an ischemic necrosis followed by revascularization and remodeling; during the ischemic and revascularization stages, the mechanical strength of the graft is diminished. Allograft supply has become a major problem, along with prevention of viral contamination, and recent data suggest that revascularization and remodeling do not occur, resulting in graft deterioration. Several research teams have reported the use of xenografts for ligament repair; however, poor experience with fixed xenografts has significantly discouraged investigators from pursuing this option.

One concept followed by several investigators is the augmentation of an autogenous graft, as opposed to complete replacement, providing temporary mechanical integrity until new tissue can assume the normal mechanical function.

The initial strength of a polymer-coated carbon fiber used to augment the iliotibial band graft exceeded that of normal tendon or ligament, and the carbon fiber became intertwined with new connective tissue as healing proceeded. Other materials, including polypropylene, have been used for augmentation of patellar tendon grafts in ligament reconstruction.

An important objective of this invention is to provide a collagen bound fabric which is used in a novel ligament repair device incorporating several key concepts; (1) the mechanical characteristics of the device will mimic those of the natural ligament and will initially be equal to or greater than normal connective tissue; (2) the surface of the implant will serve as a matrix for new tissue; (3) the femoral and tibial attachment site of the ligament prosthesis will encourage bony ingrowth; and (4) the ligament prosthesis design will take into account varying tension modes as a function of knee extension.

DACRON has been studied extensively as a possible material for the repair of tendon and ligament, and its chemical properties are well documented. DACRON was found to have low reactivity when used in intraarticular procedures. Commercial DACRON vascular grafts have been found to maintain strength for over two years. However, DACRON has been found to be subject to shear or laceration in the canine stifle joint, and the material loses tensile strength over time. It has been noted previously that fibrous tissue ingrowth to DACRON and other synthetics minimizes the internal abrasive forces, and thus decreases failure due to shear or laceration. The use of a collagen surface will enhance the growth and strength of the new fibrous tissue and therefore decrease the recovery time.

SUMMARY

One aspect of the invention is a method of bonding collagen to synthetic polyester fibers, particularly DACRON. The method comprises providing synthetic polyester fabric fibers having repeating carbonyl groups, hydrogenating the carbonyl groups, conducting a transesterification step, which includes the addition of free amine groups, reacting the free amine groups with a bifunctional crosslinking agent to produce modified polyester fibers and adding collagen to the fibers for a time sufficient to produce covalent bonding of collagen to the fibers.

The invention also includes the finished covalently bonded collagen and fiber matrix.

STATEMENT OF THE INVENTION

A. Collagen Preparation

Figure 1A:
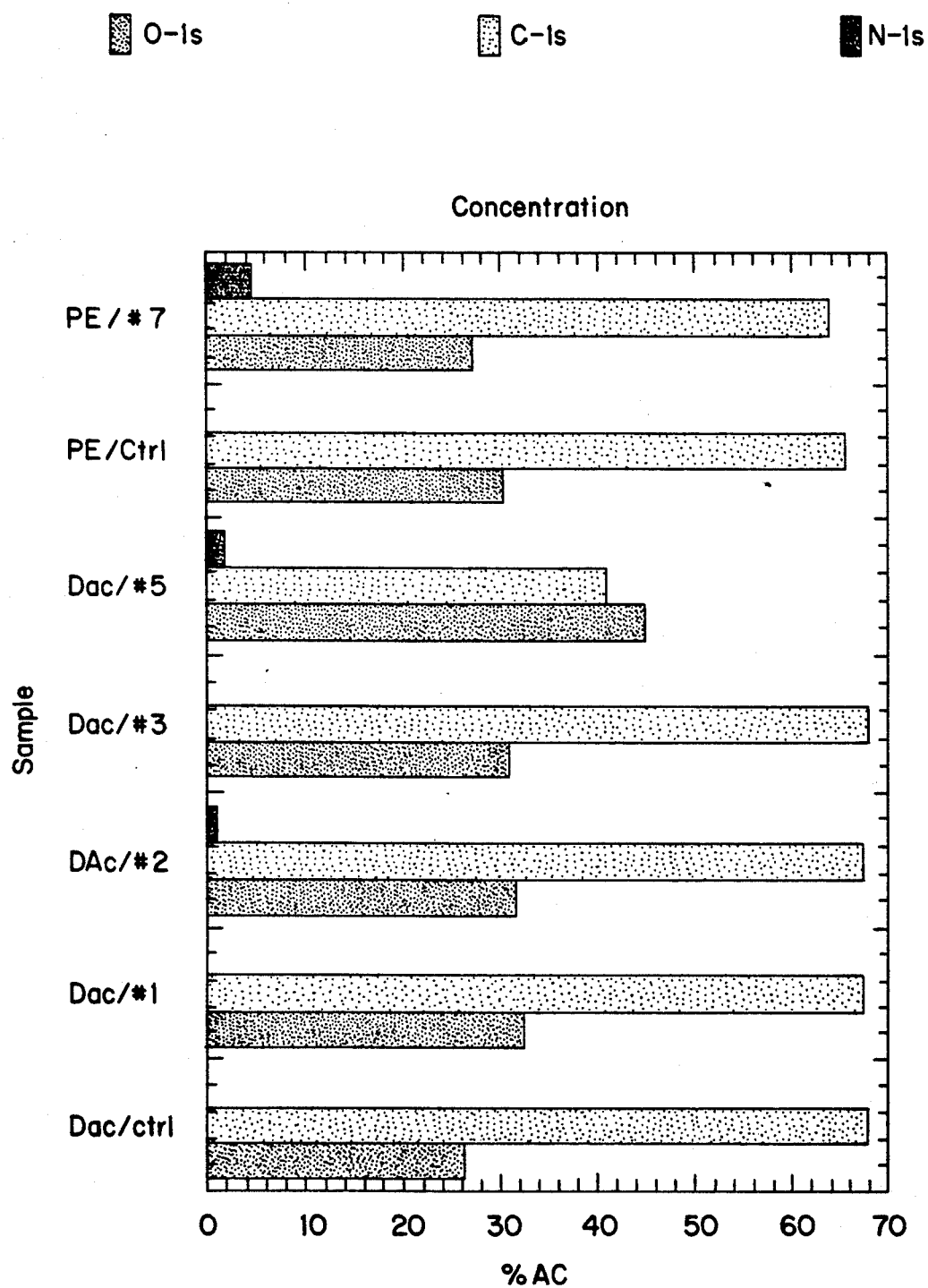
FIG. 1A is a chart showing the results of chemical treatment in accordance with the present invention.

The avian collagen used in the invention is a 1% solution (pH=3.5, 100 mM acetic acid). The avian collagen was dialyzed against 10 mM sodium acetate, 10 mM EDTA, pH 9, in a volume ratio of 1:50 for 24 hr; the dialysate was changed twice during this period. In addition to changing the pH, this dialysis procedure removed most of the divalent cations (primarily calcium), which interfere with the covalent binding of the collagen to the modified DACRON. Bovine tendon collagen was purchased from American Biomaterials as a dried powder. A 1% solution of bovine tendon collagen was made by first allowing the dried powder to swell in 100 mM acetic acid for more than 2 hrs. The dispersion was homogenized in a blender for 30 seconds and then de-aerated.

Collagen is a substance which accounts for about thirty percent of the total human body protein. Collagen, which has a characteristic amino acid composition, forms the fibrillar component of soft connective tissues such as skin, ligament and tendon, and is the major component of the organic matrix of calcified hard tissues such as bone and dentine.

There exists at least twelve genetically distinct types of collagen. The most familiar, type I, consists of three polypeptide chains. Two chains are identical and are called $\alpha 1(I)$, the third polypeptide chain being called $\alpha 2(I)$. Type I collagen forms the major portion of the collagen of both soft (skin, tendon) and hard (bone and dentine) connective tissue. Type II collagen is the major collagen of cartilage and is composed of three $\alpha(II)$ chains. Type III collagen is composed of three $\alpha 1(III)$ chains and is found in blood vessels, wounds, and certain tumors. Reticulin fibers appear to be identified with type III collagen. Basement membrane collagens are classified as type IV.

For further details as to collagen see pending application Ser. No. 07/419,496, filed Oct. 10, 1989 wherein the current applicant is also the sole inventor. The entire disclosure of said application is herein incorporated by reference.

B. Covalent Coupling of Collagen to DACRON

DACRON is a Dupont, Inc. tradename for a synthetic polyester, polyethylene terephthalate, with the following structure including repeating carbonyl groups:

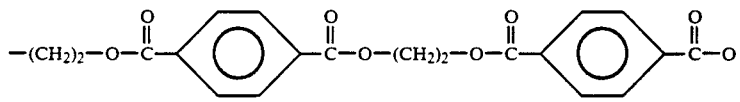

DACRON was obtained as either fiber bundles (Dupont Type 56) or as a woven textile (Leeds-Keio Ligament Device). The fiber bundles contained 40 fibers, with a fiber diameter of 10 μm. The woven textile is a porous mesh (with grid size of approximately 1 mm × 1 mm).

Reaction Step 1. Sodium borohydride, NaBH$_4$, is extensively used for the reduction of carbonyl groups and compounds to alcohols. A solution of 1 mM NaBH$_4$ in 1M NaOH was prepared, and the DACRON fibers were soaked in this solution with agitation for 1 hour. The DACRON fibers were removed and washed thoroughly with pyrogen-free water. This reaction hydrogenates the carbonyl group on either side of the phenyl ring, providing an OH group which is needed for the transesterification reaction (below).

Reaction Step 2. A transesterification reaction of the modified DACRON with phenyl carbamate produces the following structure:

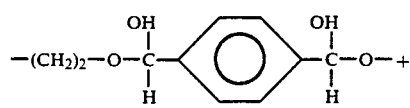

-continued

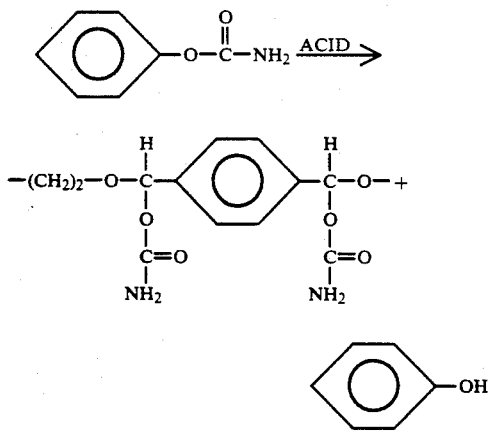

This reaction is carried out at 25° C. for 5 hours, with the DACRON immersed in a solution of phenyl carbamate in 1M HCl and 25% isopropanol.

Reaction Step 3. A bifunctional crosslinking agent is then used to react with the free amines of this modified DACRON. Dimethyl suberimidate (DMS; Pierce Chemical, Rockford, Ill.) is a water-soluble agent with two imidoester residues that react with free amines at pH 9-10. A 1-mg/ml solution of DMS in a 10 mM NaHCO$_3$ buffer, pH 9, is reacted with the modified DACRON for 24 hr. The DACRON is removed and washed thoroughly with water. This produces the following structure:

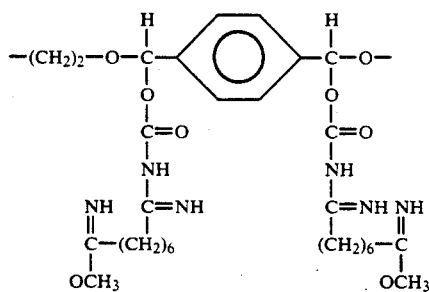

Reaction Step 4. An aqueous dispersion of 1% chicken collagen, in a pH 9, 10 mM NaHCO$_3$ buffer was reacted with the modified DACRON for 24 hours. The DACRON is removed from the dispersion and washed extensively with water to remove nonreacted collagen. Alternatively, the modified DACRON is reacted with a 1% dispersion of bovine tendon collagen, pH 3.5. The pH is then rapidly increased to pH 9 with 1M NaOH, which precipitated the collagen. The collagen was allowed to react with the modified DACRON for 24 hours. The DACRON was then washed thoroughly to remove unreacted collagen.

Surface Analysis. The products of the chemical treatments 1 through 3 were characterized by ESCA (done by Advanced Surface Technologies, Billerica, Mass.), as shown in FIG. 1A. The ESCA values of the control DACRON sample were 68% and 26%, respectively, which are reasonable values for DACRON. Upon treatment with the NaBH$_4$, the oxygen content changed to 31% and the carbon value was 67% (DACRON sample 3 in FIG. 1A). The increase in oxygen can be accounted for by the formation of some primary alcohols. The formation of primary alcohols will increase by increasing the time of borohydride reaction (DACRON sample 1 in FIG. 1A), but will not subsequently improve the ultimate collagen binding capacity. Additional borohydride treatment will also substantially degrade the strength of the DACRON fibers.

For reaction step 2, the theoretical value of carbon, oxygen, and nitrogen were calculated to be approximately 60%, 30%, and 20%, respectively; the ESCA values were 66%, 31%, and 1%, respectively (DACRON sample 2, FIG. 1A). From this result, it is reasonable to assume that the efficiency of this transesterification reaction is low; however, the trend in the changes of the atomic content numbers via ESCA confirms that the reaction did proceed (as evidenced by the presence of nitrogen).

Upon the addition of DMS (reaction step 3), the theoretical values were calculated to be 70%, 16%, and 14% for carbon, oxygen and nitrogen, respectively; the ESCA values were 66%, 30%, and 2%, respectively (DACRON sample 4, not shown in FIG. 1A). Again, the changes of the elemental content values of the sample from reaction step 2 vs. step 3 indicates that the reaction did proceed to some extent.

Reaction step 4 is characterized by the assays discussed in the next section. An alternative modification procedure was used to modify both DACRON fibers and a brand of high-density polyethylene fibers (Spectra from Allied Signal, Morristown, N.J.). The fibers were subjected to plasma treatment (Advanced Surface Technologies) using ammonia gas to produce surfaces enriched with amine residues; the ESCA analysis of plasma treated DACRON and Spectra fibers is shown in FIG. 1A (DACRON sample 5 and PE sample 7, respectively). The ESCA results confirmed that the surfaces contained nitrogen (most probably in the form of primary amines); however the amount of nitrogen for the DACRON sample was not as much as expected for this method, and the large increase of oxygen was not expected (which may be due to breakdown of the polymer, or reaction with residual oxygen gas, or a combination of both events). The fibers were then subjected to DMS treatment, as described in reaction step 3 above, which theoretically will provide a surface which will react with the acidic surface amino acids of collagen. The collagen solutions were then reacted with the plasma-treated/DMS treated fibers as described in step 4. The collagen binding to these plasma-treated fibers was analyzed via the assay described in the next section.

C. Measuring Collagen Binding 100-200 mg of each modified DACRON sample was placed in 2 ml of 12N HCl and hydrolyzed at 105° C. for 16 hours or until all the liquid evaporated; 4 ml of water was added to the vessel and heated to 90° C. for 16 hours or until all the liquid evaporated; 2 ml of water was then added to the vessel and tested for hydroxyproline using standard calorimetric methods. The precise dry weight of each sample prior to hydrolysis was recorded; the linear density of unmodified DACRON was found to be 7.97+0.64, and the chemically modified DACRON was 8.60+0.40 (see Table 2 in the section on Mechanical Testing). The amount of collagen bound under various conditions was calculated in units of micrograms collagen per milligram of DACRON, as shown in Table 1. The results of Table 1 indicate that a greater amount of collagen binds to chemically modified and plasma-treated DACRON than to the unmodified polymer. Secondly, the modified individual fiber bundles will bind a greater amount of collagen than will be woven textile, which is probably due to the greater available surface area per gram of the individual fibers. In addition, a greater amount of bovine tendon collagen binds to the modified DACRON materials than the chicken collagen. This may be due to the technique used in reaction step 4, in which bovine tendon collagen is precipitated onto the DACRON materials at pH 9, which may result in a greater amount of intramolecular collagen binding. Bovine tendon collagen binding to the plasma-treated DACRON or Spectra was equivalent to binding to the chemically modified DACRON shown in Table 1, rows D and E.

TABLE 1

Ratio of collagen to Dacron, μg collagen/mg Dacron

| | | Fiber bundles | Woven textile |
|---|---|---|---|
| A. | Unmodified Dacron with chicken collagen | 1.0 | 1.0 |
| B. | Chemically modified Dacron with chicken collagen | 4.4 | 2.1 |
| C. | Unmodified Dacron with bovine collagen | 0.5 | 0.7 |
| D. | Chemically modified Dacron with bovine collagen | 7.6 | 8.2 |
| E. | Plasma-treated Dacron with bovine collagen | 5.6 | NA |

In order to determine the resistance of the collagen coatings on the DACRON fibers to high-energy turbulence (sonication), 100–200 mg of modified DACRON samples (weighed dry to ±0.05 mg accuracy) was placed in 15 ml water. The sonicator tip was placed in the solution and run at high power for 1 min. The water was removed, and an additional 15 ml water was placed in the sonication vessel. Sonication then proceeded for 1 minute. This procedure was repeated for additional time periods of 4, 8, 15, and 30 minutes (total sonication time). Each supernatant was placed in an oven at 90° C. until all the liquid evaporated. Two milliliters of 12N HCl were added to each tube, and the supernatant samples were hydrolyzed at 105° C. for 16 hours or until all the liquid evaporated; 4 ml of water was added to vessel and heated to 90° C. for 16 hours or until all the liquid evaporated. Two milliliters of water were then added to each tube and supernatant samples were tested for hydroxyproline using standard calorimetric methods. Five DACRON sample types were tested: unmodified and modified DACRON with chicken collagen, unmodified and modified DACRON with bovine tendon collagen, and plasma-treated DACRON with bovine tendon collagen. In addition, untreated and plasma-treated Spectra fibers with bovine tendon collagen were also tested. The woven textile form of DACRON was used except for the plasma-treated samples, which were fibers.

Figure 1B:
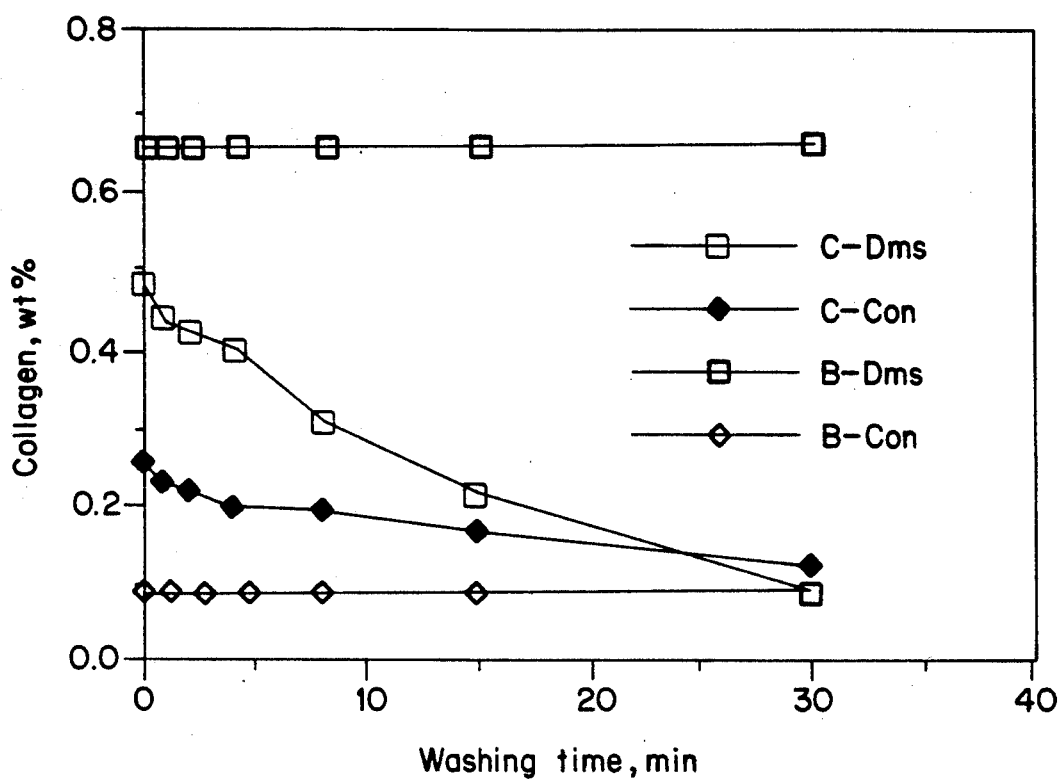
FIG. 1B is a chart showing release of collagen from modified and unmodified DACRON as a function of sonic disruption.

FIG. 1B shows that sonication will not remove the bovine tendon collagen that has been bound to the modified DACRON; conversely, very little collagen remains after the first wash of the untreated DACRON materials. However, the amount of chicken collagen bound to the modified DACRON decreases monotonically as a function of sonication time; as with the bovine tendon collagen, a large portion of the chicken collagen was removed after the first wash of the untreated DACRON materials. This greater binding capacity of the bovine tendon collagen to the DACRON materials may also be attributed to a greater amount of intramolecular collagen binding (as mentioned above). Similarly, the collagen remained bound to the plasma-treated DACRON and Spectra fibers and was removed from the untreated fibers (data not shown). Thus, either the chemical or plasma-treated modified fibers provided a reactive surface to bovine tendon collagen.

The DACRON materials were also studied using scanning microscopy (JEOL JSM T-300) to observe surface variation between the unmodified fibers vs. the collagen-coated fibers. The specimens were passed through a series of dehydrating fluids: 30% ethyl alcohol (ETOH) for 30 minutes, 50% ETOH for 1 hour, 70% ETOH for 2 hours, 80% ETOH for 2 hours, 90% ETOH for 2 hours and 100% ETOH for 3 hours. The samples were critical-point-dried using the Denton DCP-1 apparatus. The samples were sputter-coated using the Denton Vacuum Desk-1, cold-sputter-etch unit.

D. Mechanical Investigation of a Proposed Collagen-Coated DACRON Ligament Material 1. Fiber Strength This study measured the strength of treated and untreated DACRON fiber bundles in order to determine any changes resulting from chemical modification.

The procedure used in this study was derived from several standards, as follows:

ASTM Standards

ASTM D76 Specifications for Tensile Testing Machines for Textiles (vol. 7.01)

ASTM D123-89c Standard Terminology Relating to Textiles (vol. 7.01)

ASTM D1294-86 Standard Test Method for Breaking Strength and Breaking Tenacity of Wool Fiber Bundles 1-inch (25.4-mm) Gage Length (vol. 7.02)

ASTM D1774-79 Test Method for Elastic Properties of Textile Fibers (vol. 7.02)

ASTM D2101-82 Standard Test Methods for Tensile Properties of Single Man-Made Textile Fibers Taken from Yarns and Tows (vol. 7.02)

ASTM D2256-88 Standard Test Method for Tensile Properties of Yarns by the Single-Strand Method (vol. 7.01)

ASTM D2524-85 Standard Test Method for Breaking Tenacity of Wool Fibers Flat Bundle Method - ⅛-inch (3.2-mm) Gage Length (vol. 7.02)

ASTM D4849-89 Standard Terminology Relating to Yarn (vol. 7.01)

ASTM E178-80 Recommended Practice for Dealing with Outlying Observations (vol. 14.02)

ASTM F619 Practice for Extraction of Medical Plastics (vol 13.01)

ASTM F756-82 Practice for Assessment of Hemolytic Properties of Materials (vol. 13.01)

ASTM Volume Titles

1989 Book of ASTM Standards vol. 7.01; Textiles: Yarns, Fabrics, and General Test Methods 1989 Book of ASTM Standards vol. 7.02; Textiles: Fibers, Zippers 1989 Book of ASTM Standards vol. 14.02; General Test Methods, Nonmetal; Laboratory Apparatus; Statistical Methods; Appearance of Materials; Durability of Nonmetallic Materials Breaking force, elongation, initial modulus, failure modulus, and breaking toughness were investigated.

These properties, which correspond to fundamental properties widely used in the textile industry to establish limitations on yarn processing or conversion and on their end use applications, therefore fulfill the aims of this investigation.

2. Specimen Preparation

Specimens were prepared on a clean surface. Gloves were worn during specimen preparation to avoid adding skin oils to the specimen.

In order to insure reproducibility between samples within a group, each bundle of fibers was held together with surgical tape to retain its original twist. The surgical tape held the fibers in a predetermined orientation within the testing grips while providing a consistent and easily visualized gage length. Two spring-loaded hand vises equipped with rubber jaws were used to prevent fiber damage during clamping. Two strips of silastic 0.06 in. thick, 2.0 in. wide, and 7.5 cm (2.95 in.) long were used to represent a gage length ($l_o$) of 75 mm. The silastic was glued to two 0.125 in, thick rigid plates with the same dimensions as the silastic in order to provide a backing. Together, these formed two rubber "gaging pads" to consistently produce specimens with a gage length of 75 mm.

From a single spool of DACRON fiber yarn, 32 samples each 50 cm in length were cut and assigned to one of two groups at random. The control specimen was fixed in place in a 30 cm long straight container, corked at both ends, and filled with 0.9% NaCl sterile saline, with 0.1% RBS 35 detergent (Pierce) as a wetting agent, and allowed to soak for 2 hours. The containers prevented the fibers from kinking while in the medium. The specimens were taken from their containers one at a time and prepared for fixturing.

The end of each specimen was secured in a hand vise, then centered in the rubber gaging pad. Light tension was applied to the fibers, and the second gaging pad was aligned atop the first. The fibers protruded perpendicular to the free edge of the pads as the pads were clamped together. Surgical tape was applied to the protruding ends of the samples. The clamps were removed, and the specimen was placed flat in a container filled with distilled water. The mounted specimen now had a gage length of 75 mm with 25 mm of tape at either end.

Test Apparatus

Specimens were tested moist, in a standard laboratory atmosphere (20° C.), at a constant rate of extension with an Instron biaxial servohydraulic test system (Instron Series 2150, model 1321 load frame; Instron Corporation, Canton, Mass.). This system is calibrated to National Institute of Standards and Technology (NIST, formerly NBS) traceable standards. Specimens were held in place through the use of Instron pneumatic clamps (Instron Pneumatic-Action Grips, model 2712-002; Instron Corporation, Canton, Mass.). These clamps have a grip application area of 1 sq. in. and were equipped with lightly serrated loading plates "softened" with surgical tape. Two parameters were monitored: load and actuator displacement. Load was measured with an effective sensitivity of 25 N full-scale (500-N Lebow uniaxial load cell with a gain factor of ×20— Eaton Corporation, Electronic Products Division, Troy, Mich.). Displacement was measured using the Instron linear actuator's LVDT, 100-mm full-scale. Load and displacement data were acquired using Lab-Tech Notebook software (Laboratory Technologies Corporation, Wilmington, Mass.). The voltage output from the transducers were scaled within LabTech Notebook.

Test Procedure

Specimens were removed from the holding container and secured in the pneumatic grips by placing one taped end in the upper grip, assuring that the bundle was aligned along the loading axis of the test machine and that the tape edge was even and parallel with the grip face. Once properly aligned, the pneumatic jaws were drawn closed and alignment checked again. The lower grips were then brought into position and the second taped end installed in the grips. The sample was loaded to failure at a constant elongation rate of 10% per second (7.5 mm/sec).

Calculations

The following quantitites were investigated:

Breaking force ($F_b$, N): the force required to break the specimen. It is read directly from the data file and recorded. Elongation (d, mm): the change in length of specimen.

Linear density (T, tex): computed for each tested sample by allowing it to air-dry in the standard laboratory atmosphere for 24 hours and then weighing. The gram mass was measured on an analytical balance (Sartorius model R160D Analytical Balance; Sartorius Research, Bohemia, N.Y.) recorded to the nearest 0.02 mg. divided by the gage length (75 mm), and multiplied by $10^{66}$ mm/km to obtain linear density in tex (g/km).

Stiffness (K, N/mm): the slope of the initial straight line region of the load-displacement curve in:

$M = DF/Dd$

Breaking toughness ($U_b$, mJ): the energy required to break the specimen. This quantity corresponds to the area under the load-displacement curve.

RESULTS AND DISCUSSION

Mean and standard deviation values for breaking load, breaking elongation, initial stiffness, failure stiffness, and breaking toughness were computed for each set of treated and untreated specimens. Student's t-test was performed comparing treated with control to confirm the null hypothesis that samples do not differ in these characteristics at the level of significance $p < 0.05$. This information is reported in Table 2.

TABLE 2

| | | Fiber strength of treated vs. untreated (control) Dacron | | | | | |
|---|---|---|---|---|---|---|---|
| Sample | n | Linear density (tex) | Initial stiffness (N/mm) | Breaking force (N) | Breaking toughness (mJ) | Elongation to failure (mm) | Failure stiffness (N/mm) |
| Treated | 16 | 8.60 ± 0.40* | 0.91 ± 0.12* | 7.83 ± 0.48 | 103.6 ± 33.7 | 18.8 ± 4.3 | 0.42 ± 0.08 |

TABLE 2-continued

| | | Fiber strength of treated vs. untreated (control) Dacron | | | | | |
|---|---|---|---|---|---|---|---|
| Sample | n | Linear density (tex) | Initial stiffness (N/mm) | Breaking force (N) | Breaking toughness (mJ) | Elongation to failure (mm) | Failure stiffness (N/mm) |
| Control | 8 | 7.97 ± 0.64 | 1.05 ± 0.08 | 7.97 ± 0.19 | 112.9 ± 25.2 | 20.0 ± 3.3 | 0.40 ± 0.06 |

*p < .05.

The initial stiffness is a measure of resistance to stretch in the low-strain region of the loading cycle. This parameter is of specific interest, as the majority of the work performed by the ligament prosthesis will be done over this initial region. The data in Table 2 indicate that there is a statistically significant difference (using $p<0.05$) between the chemically treated and control (untreated) DACRON fiber bundles, the difference being about 13%. This change in stiffness will be discussed further in the next section describing the variation in relaxation behavior of the DACRON as a function of chemical treatment. On the other hand, there was no significant difference between the breaking force, breaking toughness, elongation, or failure modulus of the untreated versus treated DACRON. These parameters are all considered fundamental properties of the strength of the fiber bundles; therefore, these data suggest that there is no measurable degradation of the fiber strength due to the chemical processing. Lastly, it should be noted that the linear density of the DACRON increases upon chemical modification and subsequent collagen binding. This change is somewhat expected, as the collagen adds extra mass to the fibers; the change in linear density due to collagen binding does not directly affect the mechanical properties of the fibers. Therefore, mechanical parameters that are sensitive to linear density are not relevant.

Study Concerning Variation in the Relaxation Behavior of DACRON Fiber Bundles as a Function of Chemical Modification The procedure which is to be followed is based on American Society for Testing Materials (ASTM) standard D1774-79 entitled "Test Method for Elastic Properties of Textile Fibers." The use of a textile standard was based on experience in the textile industry, with determination of changes in yarn elastic properties as a result of various bulking, coloring, texturing, and kinking processes. These affect the fiber's ability to recover from tensile deformation and therefore on the procedures and processes that can be used and the items that can be fabricated following such processing.

The test is designed to give information about the elastic behavior of the material at both large and small deformations, which spans the physiological range and the incorporates that range where trauma might be expected to occur.

MATERIALS AND METHODS

The chemically modified and control specimens were divided equally and assigned to one of three groups representing three maximum elongation values, 2%, 5%, and 10%. Samples were prepared as explained in the previous section, with the exception that the fiber length was 200 mm.

Test Procedure

Group 1. Specimens were loaded under constant displacement at the rate of 10%/min, (20 mm/min) until they reached 2%. The crosshead was held at 2% for 60 seconds while stress was allowed to relax. The specimen was then unloaded to the original gage length and held for 180 seconds, in which time the specimen was allowed to return to its original length. The specimen was then reloaded to the original 2% point and unloaded immediately. The specimen was then unmounted and discarded.

Group 2. The above procedure was repeated except the specimen was extended 5%.

Group 3. The above procedure was repeated except the specimen was extended 10%.

Calculations

Energy recovery (%): energy recovered after loading and unloading of the specimen after the initial plastic deformation cycle. Values are expressed as percent of loading energy.

Permanent deformation energy loss(%): the energy lost during the plastic deformation of the specimen. It is measured by subtracting the area under the second loading curve from the area under the initial loading curve. Values are expressed as a percentage of original loading energy.

Plastic deformation (%): that part of the total elongation not recovered by the specimen following unloading. This is calculated by measuring the difference between the original, or gage length and the zero load length of the specimen at the beginning of the second loading cycle. Expressed as a percentage of original length (200 mm).

Relaxation (N): the decrease in load measured during the 60 sec that the specimen is held at a constant elongation. This relaxation is seen on the load-deformation curve as the vertical line connecting the initial loading and unloading curves.

RESULTS AND DISCUSSION

The relaxation properties of the modified and unmodified DACRON fiber bundles (energy recovery, permanent deformation, plastic deformation, and relaxation), in addition to the initial modulus of the study in the previous section, provide some indication of the stretch behavior of the material during elongation. While the ligament prosthesis is expected to operate primarily in the physiological range of 0-5% elongation, it is possible that traumatic injury may force the device to operate at regions of 10% or higher; therefore, both ranges were investigated in this study.

As can be seen from Table 3, there were statistically significant differences between the unmodified (control) DACRON fiber bundles and the modified (treated) samples for permanent and plastic deformation. This correlates with the differences observed for the initial modulus (Table 2) between the control and treated samples, as the properties of stretch and stiffness have been altered due to the chemical modification of the fiber bundles. It is unknown how these changes would affect the function of the proposed ligament prosthesis; it is assumed, however, that the collagen coating would provide a more compatible surface for cell attachment. Both the cell culture and animal studies described in subsequent sections support this hypothesis.

It is also assumed that the improved biological response will lead to improved characteristics of new fibrous tissue production, a hypothesis which is also supported by the studies reported here; the production of new, organized fibrous tissue would provide additional support to the synthetic fibers and may compensate for any difference between the mechanical properties of the synthetic ligament device and the native tissue. A function of further studies will be to test these hypotheses using the constructed devices implanted in the knee. Alternatively, the differences observed for the parameters of initial modulus and plastic and permanent deformation may have been a result of the testing protocol. The collagen coating on the modified DACRON fiber may have altered the surface in such a way as to cause a slight slippage of the fibers in the grips; this hypothesis is supported by the fact that the parameters of energy recovery and relaxation for the unmodified vs. modified DACRON are not significantly different, although the parameters of deformation are significantly different.

relative plating density was determined for four samples: an empty control (support without DACRON), a DACRON control (unmodified woven textile), modified DACRON with collagen (using glutaraldehyde as a crosslinking agent), and modified DACRON with collagen (using DMS as a crosslinking agent).

Figure 2A:
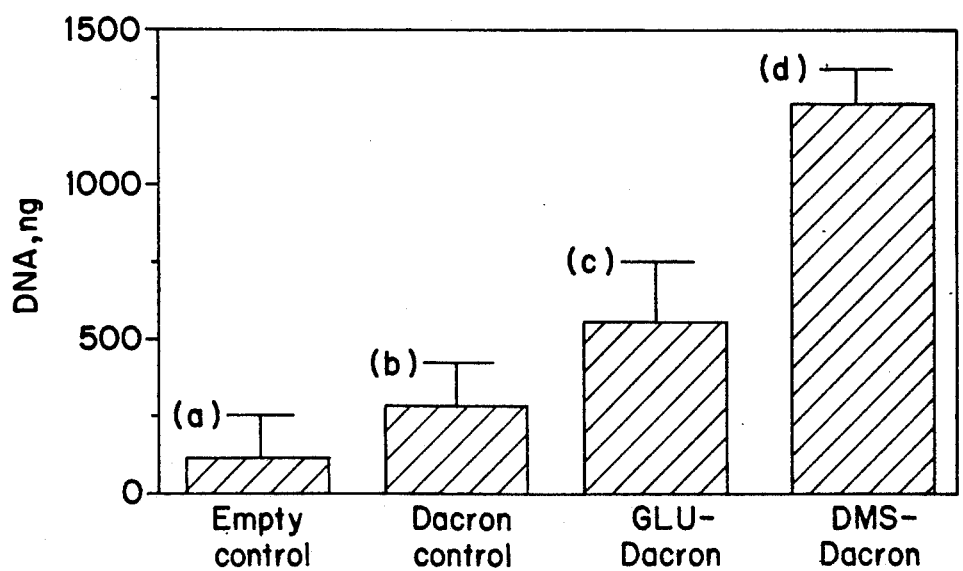
FIG. 2A shows cell binding (plating density on samples after 4 hours in cell culture as measured by DNA concentration)

As can be seen in FIG. 2A, the plating density (cell binding measured at 4 hours) of the samples with collagen are significantly greater than the unmodified DACRON sample. In addition, cell binding to the modified DACRON with collagen using DMS as a crosslinking agent is greater, by a factor of $>2$, than the sample using glutaraldehyde as a crosslinking agent; this is somewhat expected, as it has been reported previously that the use of aldehyde agents to crosslink collagen will decrease cell compatibility. (It should be noted that this DACRON textile is a very porous mesh, with relatively few cells binding to the fibers; it is therefore important to compare the cell density of these untreated and treated DACRON meshes as opposed to what one might expect for a nonporous 1-cm sample.)

Figure 2B:
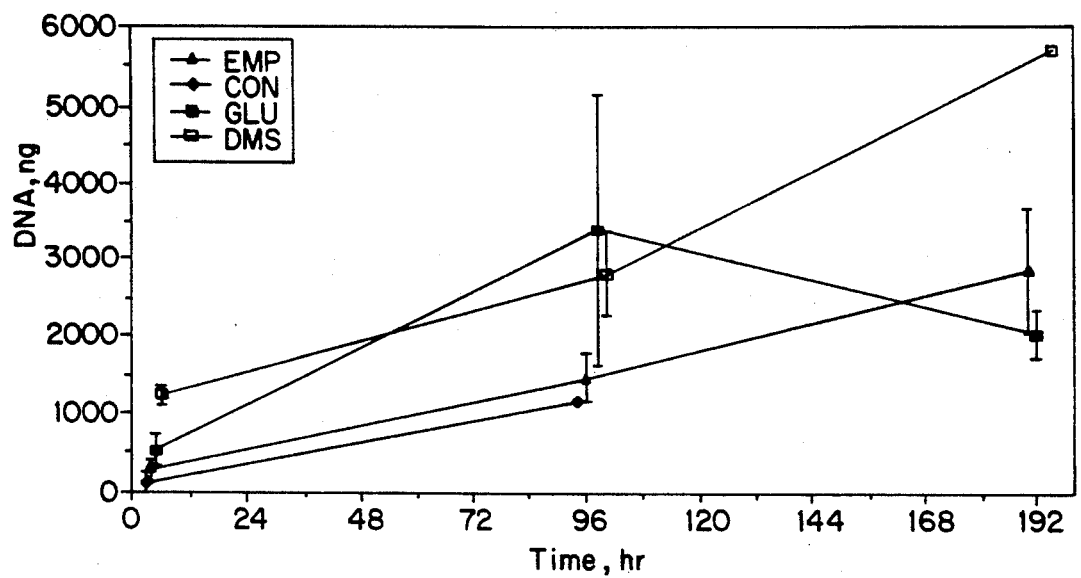
FIG. 2B shows cell growth as measured by the four samples of FIG. 2A.
Figure 3:
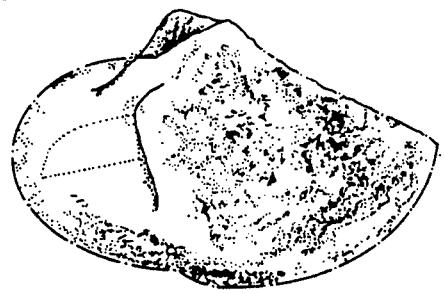
FIGS. 3 and 4 show respectively the area of origin of the anterior cruciate ligament on the lateral condyle of the left femur and the area of insertion of the anterior cruciate ligament on the proximal surface of the left tibia.

FIG. 2B exhibits the results of cell growth on the four samples and controls as a function of time (4 hours, 4 days, and 8 days). As can be seen, the modified DACRON with collagen (using DMS as a crosslinking

TABLE 3

| Variation in the relaxation behavior of treated vs. untreated Dacron fiber bundles | | | | | | |
|---|---|---|---|---|---|---|
| Sample | Original elongation | n | Energy recovery (%) | Permanent deformation energy loss (%) | Plastic deformation (%) | Relaxation (N) |
| Treated | 2% | 7 | 83.0 ± 5.3 | 0.28 ± 0.11* | 0.40 ± 0.44 | 2.60 ± 0.48 |
| Control | 2% | 8 | 85.0 ± 4.9 | 0.14 ± 0.03 | 0.08 ± 0.08 | 2.26 ± 0.34 |
| Treated | 5% | 8 | 54.9 ± 2.2 | 0.35 ± 0.04* | 1.01 ± 0.11* | 0.71 ± 0.17 |
| Control | 5% | 8 | 55.8 ± 2.7 | 0.28 ± 0.02 | 0.68 ± 0.08 | 0.55 ± 0.14 |
| Treated | 10% | 8 | 47.4 ± 2.1 | 0.68 ± 0.06* | 4.58 ± 0.72* | 1.10 ± 0.20 |
| Control | 10% | 8 | 49.7 ± 2.1 | 0.61 ± 0.05 | 3.92 ± 0.40 | 0.90 ± 0.18 |

*$p < .05$.

Cell Culture Studies

The growth of fibroblasts on unmodified vs. modified DACRON was investigated using a porous woven textile. In this series of experiments, the porous woven textile was secured to a round plastic support having an opening of 1 cm in diameter. The support and textile were sterilized by agitation in ethanol for 24 hours and dried under ultraviolet light immediately before use. Fibroblasts were obtained from the hindfoot superficial extensor tendons from 14 day-old male rats. The tendons were removed under sterile conditions using a surgical microscope. The cultures were grown in Dulbecco's Modified Eagle's Medium containing 10% fetal bovine serum and 1% penicillin-streptomycin. They were maintained at 37° C. in a humidified incubator in an atmosphere consisting of 95% filtered air and 5% filtered $CO_2$. Once the stock cultures were confluent (1 million to 2 million cells per 60 mm culture plate), trypsin was used to remove the cells using standard methods.

The woven textile samples were placed in 60-mm dishes, and a cell solution of 1.5 million cells/ml was placed in the dishes and assayed according to standard procedures. Cell density was determined by removing and rinsing with buffer sample support and placing it in a clear culture dish with enough distilled water to cover the sample. The bound cells were disrupted and homogenized using an ultrasonic probe. The supernatant was lyophilized and reconstituted in the DNA assay buffer and assayed according to standard procedures. The agent) shows the greatest rate of cellular growth. At 96 hours, there is greater growth (by a factor $>2$) on the collagen-coated vs. untreated DACRON mesh. At 120 hours, the fibroblasts on the collagen-coated, DMS crosslinked DACRON mesh had at least a 4-fold greater growth rate than the untreated DACRON mesh. There is a substantial improvement in cell binding, cell morphology, and cell growth on the modified DACRON with collagen versus the unmodified DACRON samples, as can be seen from these micrographs.

Tendon fibroblasts were cultured on untreated DACRON fibers, chemically treated, collagen-coated DACRON fibers, untreated Spectra fibers, and plasma-treated, collagen-coated Spectra fibers using the previously described techniques. The cells were observed to aggressively attach and form colonies on all types of fibers, indicating that the treatment produced no cytotoxic effects. The outgrowth rates (colony formation rates) of the cells, taken over a 7-day period, cultured on these fibers are shown in Table 4.

TABLE 4

| Fiber outgrowth rates | | | |
|---|---|---|---|
| | Outgrowth rate | | |
| Fiber | μm/date | S.D. | n |
| A. Dacron | 862.47 | 739.12 | 66 |
| B. Chemically modified/ bovine collagen Dacron | 1526.84 | 966.82 | 46 |
| C. Plasma-treated bovine collagen Dacron | 1314.72 | 429.84 | 55 |
| D. Spectra | 966.96 | 253.58 | 37 |

TABLE 4-continued

| | Fiber outgrowth rates | | |
|---|---|---|---|
| | | Outgrowth rate | |
| Fiber | μm/date | S.D. | n |
| E. Plasma-treated/ bovine collagen Spectra | 1161.84 | 168.60 | 44 |

The outgrowth rate of cells grown on the chemically treated, collagen-coated DACRON was 77.1% higher than that of the control fibers. This represented the largest difference in growth of any types of fibers examined to date. While the control DACRON outgrowth rate was comparable to rates previously reported for other DACRON fibers, the rates recorded on the collagen-coated fibers were the highest recorded on any fiber type to date. A student's t-test determined the rate difference to be significant to a $p<0.001$ level.

Preliminary Results

Hydroxyapatite (HA) deposition on collagen-coated DACRON fibers

A procedure was developed for the deposition and growth of hydroxyapatite (HA) on the collagen (chicken or bovine) coatings bonded to DACRON fibers. The rationale here is that the HA coating will act as a nucleation substrate for physical-chemical deposition of in vivo HA. It is anticipated that this newly deposited HA will then facilitate strong attachment of the fiber to the bone, simulating the normal ligament attachment in vivo.

A metastable solution at pH 7.4 of $Ca^{+2}$ and $PO_4^{-2}$ was prepared from $CaCl_2$ and $Na_2HPO_4$, which would normally not precipitate HA in 24 hours or longer. The collagen-coated DACRON fibers are immersed in the Ca $PO_4$ solution for 15 minutes, removed and allowed to air-dry. This creates a thin, sparse HA coating that can act as a nucleating template for further HA growth. At this point the dry fibers are immersed again in the metastable Ca $PO_4$ solution for 24 hours, removed and allowed to air-dry. SEM photographs of the fibers after 24 hours show large particles on the outside with a finer, more uniform coating closer to the fiber surface. Elemental analysis of particles of various sizes using the Kevex x-ray microanalysis system with micrometer range resolution showed significant Ca and P peaks in a ratio indicative of HA. This indicates that the coating is in fact calcium phosphate.

This technique of HA deposition will enable us to vary crystal size and perfection $CO_3$ content, and F content by varying Ca, $PO_4$, $CO_3$, and F concentrations in solution along with solution temperature. By altering HA solubility and reactivity with these parameters, the optimum HA coating on the collagen-coated DACRON fibers can be achieved to maximize the attachment strength to bone.

Intraoperative Bone Anchorage

Although long-term it is anticipated that bone attachment to the fibers (e.g., utilizing the hydroxyapatite deposition procedure described in a. above) will anchor the ligament prosthesis, an intraoperative anchorage system must be established that can survive the early rehabilitation period until bone attachment occurs. With this objective in mind, experiments were performed with a harpoon-shaped suture anchor, the Mitek GII Anchor (Mitek Surgical Products Inc., Norwood, Mass.). The anchors are implanted in bone after the drilling of a 2 mm diameter hole. After insertion, the nitinol "harpoons" expand and lock the device in cancellous bone. Anchors were implanted in the femoral and tibial attachment sites of the ACL and pull out tests were performed with an Instron model 1321 mechanical properties testing machine at a crosshead speed of 1 mm/sec. In the femoral attachment site the average pullout strength was found to be 110N and in the tibial attachment site an average pullout strength of 170N was attained. Since it is anticipated that a multi-banded device will be used, it appears that adequate initial attachment strength can be achieved with such anchors that can be rapidly implanted with minimal bone trauma.

Conclusion

The chemical modification procedure was previously optimized for collagen binding while minimizing any changes in fiber strength. Results from the study showed that various crosslinking protocols (e.g., glutaraldehyde vs. DMS) had no effect on collagen binding or fiber strength. However, there were changes in the amount and tenacity of collagen binding to the DACRON with bovine vs. chicken collagen (see Table 1 and FIG. 1). This may be due to the difference in binding technique (reaction step 4) of bovine versus chicken collagen, which was necessitated by the different solubility properties of these two Type I collagens.

In addition, there was less collagen binding to the DACRON woven textile (Leeds-Keio device) versus the fiber bundles. This effect was most likely due to the decreased available surface area per gram of DACRON of the woven textile versus the fiber bundles. An alternative surface modification procedure was proposed and tested (using plasma treatment). It is our intention to pursue the plasma surface treatment and to attempt to optimize the collagen binding to the amine-derivative surfaces. Preliminary disruption studies suggest that the treatment will lead to the strong binding of bovine tendon collagen on the DACRON or Spectra fiber surfaces, as opposed to the loose, nonspecific binding that occurs on the untreated surfaces.

Figure 4:
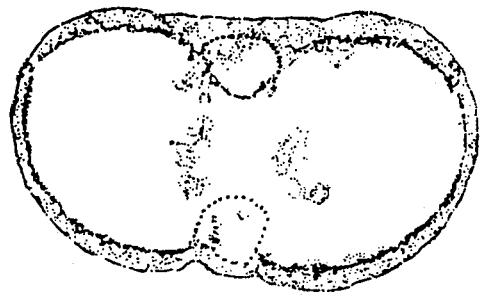

The cell culture experiments confirmed the hypothesis that collagen-coated DACRON fibers provide greater cell-binding capacity and improve cell growth when compared to uncoated fibers. The scanning electron micrographs of FIG. 4 clearly showed a stronger cellular response and connective tissue formation on the collagen-coated DACRON fibers versus the uncoated DACRON fibers. We attempted to assay collagen production directly via a pulse-chase experiment (using radiolabeled proline along with a quantitative determination of the hydroxyproline/protein ratio), but were unsuccessful due to the small quantities of protein formed on the DACRON mesh (as the number of cells which adhere to the DACRON mesh was small). However, there were indications from the radiolabeled proline results, that cells grown on the collagen-coated DACRON samples indeed produced more protein than those grown on the uncoated DACRON samples (normalizing for the difference in cell numbers). The cell culture studies also confirmed that glutaraldehyde crosslinking was less biocompatible than DMS crosslinking.

Mechanical testing of the treated versus untreated fibers showed that there was little change in fiber strength upon modification. However, certain parameters of relaxation and stretch did show a statistically significant difference between the treated and untreated fiber bundles. It is possible that the improved cellular response to the collagen-coated fibers would compensate for these changes. However, we are currently investigating collagen coating an alternative synthetic polymer, and testing for differences in fiber strength and relaxation. It is also possible that the observed differences were due to the testing protocol. We are currently testing this hypothesis by investigating the mechanical properties of chemically modified DACRON fiber bundles without collagen coating vs. unmodified samples.

Thus, there is set forth herein the initial success in the anchoring studies and the hydroxyapatite-coated fibers (to be used on the prosthesis ends for proper bone attachment). The anchors are commercially available, and can be attached directly to the fibers. The anchor strength was tested directly in a human cadaver femoral condyle, with the anchor near the native anterior cruciate ligament attachment point. In addition, a method was developed to precipitate calcium hydroxyapatite directly onto the collagen-coated DACRON fibers. It is anticipated that this coating will be efficacious for bone ingrowth in the prosthesis, and hence establish a strong bond.

Finally, the animal biocompatibility studies indicated that the collagen coatings on the DACRON fiber bundles improved cellular response by (1) decreasing giant cell activity; (2) improving fibroblast response; and (3) increasing collagen production.

ADDITIONAL EXPERIMENTAL DESIGN AND METHODS

All previous attempts at anterior cruciate ligament (ACL) reconstruction using devices with strength and stiffness comparable to the natural ACL have unacceptably high failure rates because of stretching out and occasional frank failure. This has been the case whether the device consisted of synthetic fibers or processed biological tissue. An investigation of the mechanics of these devices versus the structure of the natural ACL leads to a greater understanding of the reasons for these failures. First, the ACL is not a uniaxial structure. It is a multisegmented structure, approximately 35 mm long and 22 mm wide, whose segments are loaded in different partitions of the total range of motion of the knee. The ACL is surrounded by a mesentery-like fold of synovium that originates from the posterior intercondylar area of the knee and completely envelopes the ACL and the posterior cruciate ligament. Thus, while the cruciate ligaments are intraarticular, they are also extrasynovial. The areas of origin of the cruciate ligaments are shaped approximately like sectors of ellipses. The area for the origin of the ACL on the lateral condyle is limited posteroproximally by an elliptical arc, anterodistally by a long semichord, and anteroproximally by a short semichord. The area for the insertion of the ACL has approximately the shape of an equilateral triangle with rounded corners; one side of which is situated near the middle of the anterior intercondylar area and runs nearly parallel to its anterior margin. The opposite corner is close to the tip of the intercondylar eminence. The area of origin is more than twice as large as the area of insertion.

Many authors have described anatomically separate bands the ACL. The bands are called anteromedial and posterolateral, with some including an intermediate band. However, Fuss has found that when the cruciate ligaments were split into bundles, preformed division into smaller units was not apparent. Nevertheless, he was able to relate positions within the area of origin to those in the area of insertion. For example, the fibers originating most anteriorly are seen to be inserted most anteriorly, and those originating most posteriorly are inserted most posteriorly. He also determined that the individual fibers of the ligament have different lengths.

For certain fiber bundles of the ACL, the distance from origin to insertion does not change during flexion and extension. These portions of the ACL have been named "guiding bundles" by Fuss. The origin and insertion of the guiding bundles is most anterior in their respective attachment areas. For all other fiber bundles of the ligament, the distances between the points of origin and insertion change in flexion and extension; therefore, in some positions certain fiber bundles are taut, while in other positions they are relaxed.

Considering the function of the greatest portion of the bundles of the ACL, the opinion of most authors is that the main function of the ACL is to limit extension. The extension-limiting bundles of the ACL are situated mainly posteromedially.

The present invention accordingly provides a novel method to produce a fabric matrix which is to be used ligament prosthesis design which incorporates key concepts to improve ligament repair, including: 1) mechanical characteristics which are initially equal to or greater than normal connective tissue; and 2) a surface matrix which will encourage new tissue growth (due to a covalently-bound collagen coating).

In conclusion it will be seen that with the present invention there is a chemical treatment procedure to bind collagen covalently to DACRON, a synthetic fiber used extensively in implantable medical devices. There is an observed increase in cell attachment and fibroblast growth on the collagen-coated DACRON versus the uncoated fibers. In addition, an in vivo biocompatibility assay was used to compare the coated with the uncoated DACRON fibers; it was found that the collagen coating improved the cellular response of the implant. The product of the present invention can be used in prostheses as well as where DACRON has been previously used in medical devices and other prosthesis, such as vascular prostheses.

Without further elaboration, the foregoing will so fully illustrate my invention that others may, by applying current or future knowledge, readily adapt the same for use under various conditions of service.

I claim:

1. A method of covalent bonding collagen to DACRON fibers, said method comprising providing DACRON fibers having repeating carbonyl groups, hydrogenating said repeating carbonyl groups, conducting a transesterification step which includes the addition of free amine groups, reacting the free amine groups with a bifunctional crosslinking agent to produce modified DACRON and adding collagen to said modified DACRON fibers for a time sufficient to produce covalent bonding of collagen of said fibers.

2. The method of claim 1 wherein said hydrogenating is accomplished by a reduction of the carbonyl groups in said DACRON, utilizing sodium borohydride as the reduction agent.

3. The method of claim 1 wherein said transesterification step is carried out with phenyl carbamate and wherein the free amines added in the transesterification step are reacted with dimethyl suberimidate.

4. The method of claim 1 wherein said collagen is selected from the group consisting of chicken collagen and bovine tendon collagen.

5. The method of claim 4 wherein said chicken collagen is provided in an aqueous dispersion at a concentration of 1% by weight, at a pH 9, 10 mM NaH CO$_3$ buffer and wherein said dispersion is reacted with said DACRON for 24 hours.

6. The method of claim 4 wherein said bovine tendon collagen is provided in a dispersion at a concentration of 1% by weight, at a pH of 3.5 which is rapidly increased to pH 9 with 1M NaOH to precipitate collagen which is then reacted with said DACRON for 24 hours.

7. A fabric matrix comprised of fibers and collagen being covalently bound to said fibers in accordance with the method of claim 1.

8. The fabric matrix of claim 7 utilized in ligament prosthesis design.

* * * * *